United States Patent
Williamson, IV et al.

(10) Patent No.: US 6,659,270 B2
(45) Date of Patent: Dec. 9, 2003

(54) NON-KINKING AND NON-TANGLING SUTURE PACKAGE

(75) Inventors: Warren P. Williamson, IV, Loveland, OH (US); Craig B. Berky, Milford, OH (US); Paul A. Spence, Louisville, KY (US); Mark Ortiz, Milford, OH (US)

(73) Assignee: IDX Medical, Ltd., Loveland, OH (US)

( * ) Notice: Subject to any disclaimer, the term of this patent is extended or adjusted under 35 U.S.C. 154(b) by 0 days.

(21) Appl. No.: 10/200,398

(22) Filed: Jul. 22, 2002

(65) Prior Publication Data

US 2002/0175091 A1 Nov. 28, 2002

Related U.S. Application Data

(63) Continuation of application No. PCT/US01/02772, filed on Jan. 26, 2001.
(60) Provisional application No. 60/178,577, filed on Jan. 28, 2000.

(51) Int. Cl.$^7$ .............................................. A61B 17/06
(52) U.S. Cl. ...................................... 206/63.3; 206/380
(58) Field of Search .............................. 206/63.3, 380, 206/482, 483, 495

(56) References Cited

U.S. PATENT DOCUMENTS

| | | |
|---|---|---|
| 2,225,833 A | 12/1940 | Horine |
| 2,590,799 A | 3/1952 | Solowey |
| 2,870,906 A | 1/1959 | Harkness et al. |
| 3,444,994 A | 5/1969 | Kaepernik et al. |
| 3,857,484 A | 12/1974 | Thyen |
| 3,876,068 A | 4/1975 | Sonnino |
| 3,985,227 A | 10/1976 | Thyen et al. |
| 4,089,409 A | 5/1978 | Cerwin |
| 4,121,711 A * | 10/1978 | Bolanowski ............. 206/63.3 |
| 4,168,000 A | 9/1979 | MacRitchie |
| 4,260,056 A | 4/1981 | Horvath et al. |
| 4,261,463 A | 4/1981 | Shave |
| 4,961,498 A | 10/1990 | Kalinski et al. |
| 4,969,893 A | 11/1990 | Swor |
| 5,052,551 A | 10/1991 | Cerwin et al. |
| 5,078,730 A | 1/1992 | Li et al. |
| 5,101,968 A | 4/1992 | Henderson et al. |
| 5,123,528 A | 6/1992 | Brown et al. |
| 5,131,534 A | 7/1992 | Brown et al. |
| 5,154,283 A | 10/1992 | Brown |
| 5,246,104 A | 9/1993 | Brown et al. |
| 5,271,495 A | 12/1993 | Alpern |
| 5,386,912 A | 2/1995 | Holzwarth et al. |
| 5,427,243 A | 6/1995 | Roshdy |
| 5,435,438 A | 7/1995 | Scanlon |
| 5,472,081 A | 12/1995 | Kilgrow et al. |
| 5,529,175 A | 6/1996 | Brunken |
| 5,566,821 A | 10/1996 | Brown et al. |
| 5,575,382 A | 11/1996 | Sobel et al. |
| 5,623,810 A | 4/1997 | Dey et al. |
| 5,655,652 A | 8/1997 | Sobel et al. |
| 5,661,954 A | 9/1997 | Ivanov et al. |
| 5,675,961 A | 10/1997 | Cerwin et al. |
| 5,695,138 A | 12/1997 | Daniele et al. |
| 5,709,067 A | 1/1998 | Dey et al. |
| 5,715,942 A | 2/1998 | Li et al. |
| 5,799,788 A | 9/1998 | Webb |
| 5,827,324 A | 10/1998 | Cassell et al. |
| 6,029,806 A | 2/2000 | Cerwin et al. |
| 6,260,696 B1 * | 7/2001 | Braginsky et al. ......... 206/63.3 |
| 6,260,699 B1 * | 7/2001 | Kaplan et al. ............ 206/63.3 |

* cited by examiner

*Primary Examiner*—Luan K. Bui
(74) *Attorney, Agent, or Firm*—Wood, Herron & Evans, L.L.P.

(57) ABSTRACT

A suture package (30) including a panel having a series of superimposed subpanels (32*a*). A suture (20) loops back and forth on the subpanels (32*a*) such that adjacent loops are retained on adjacent subpanels (32*a*) and the adjacent subpanels separate the adjacent loops from one another. In the preferred embodiment, an accordion style panel (32) is utilized and the series of subpanels (32*a*) are folded into a superimposed relationship. Various features are incorporated to reduce the instances or likelihood of kinking and tangling of the suture (20) when pulled from the package (30) by a user.

37 Claims, 7 Drawing Sheets

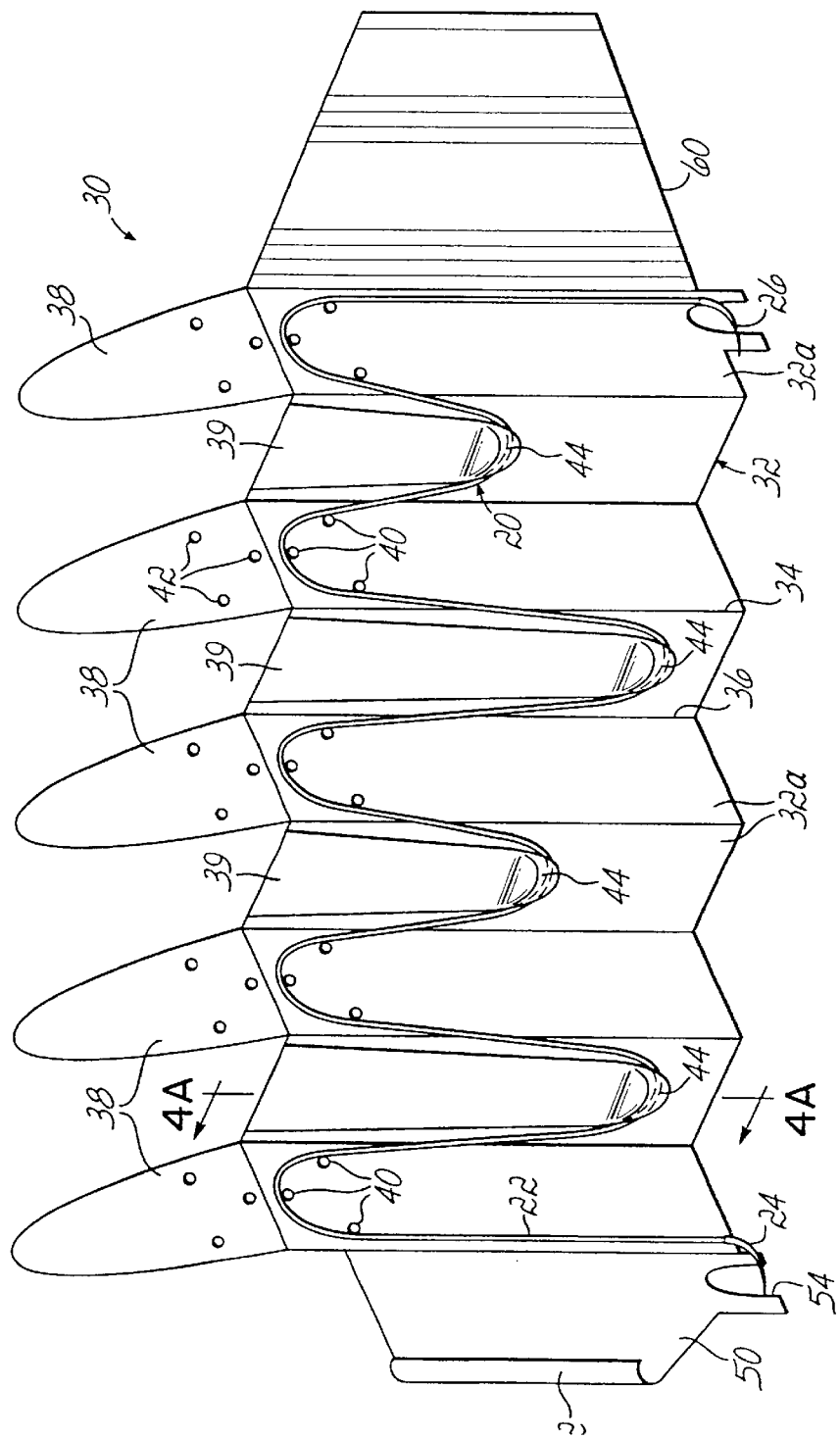
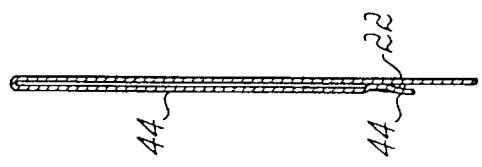

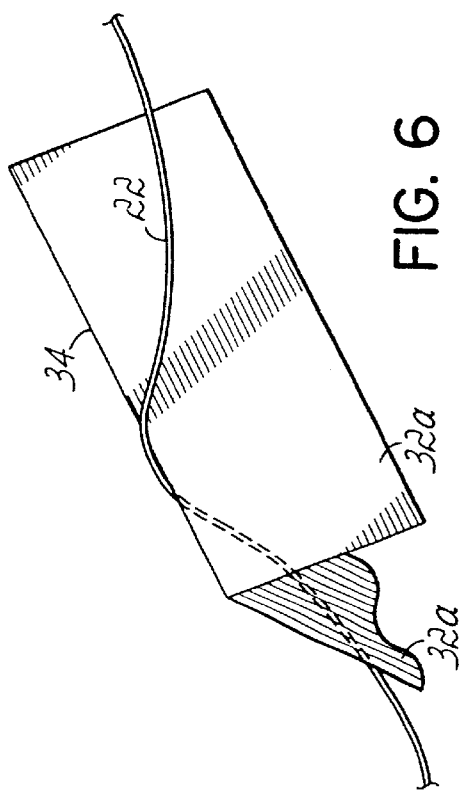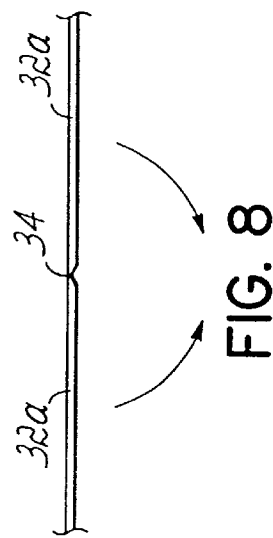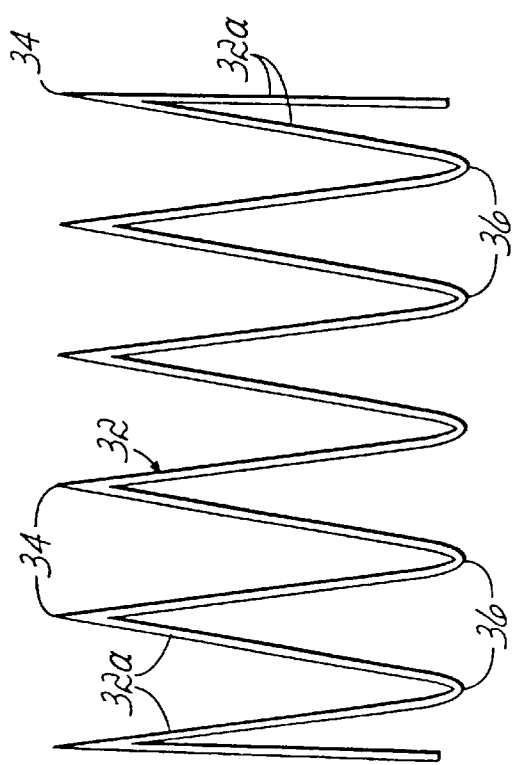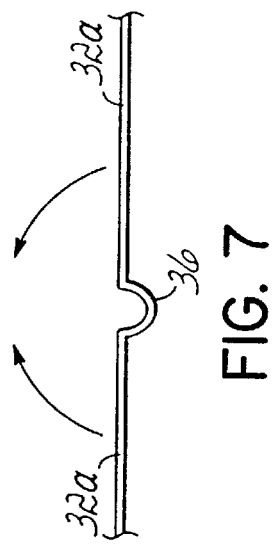
FIG. 6
FIG. 8
FIG. 5
FIG. 7

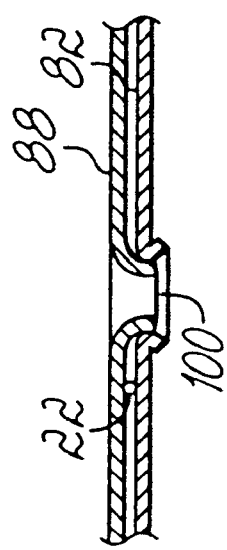
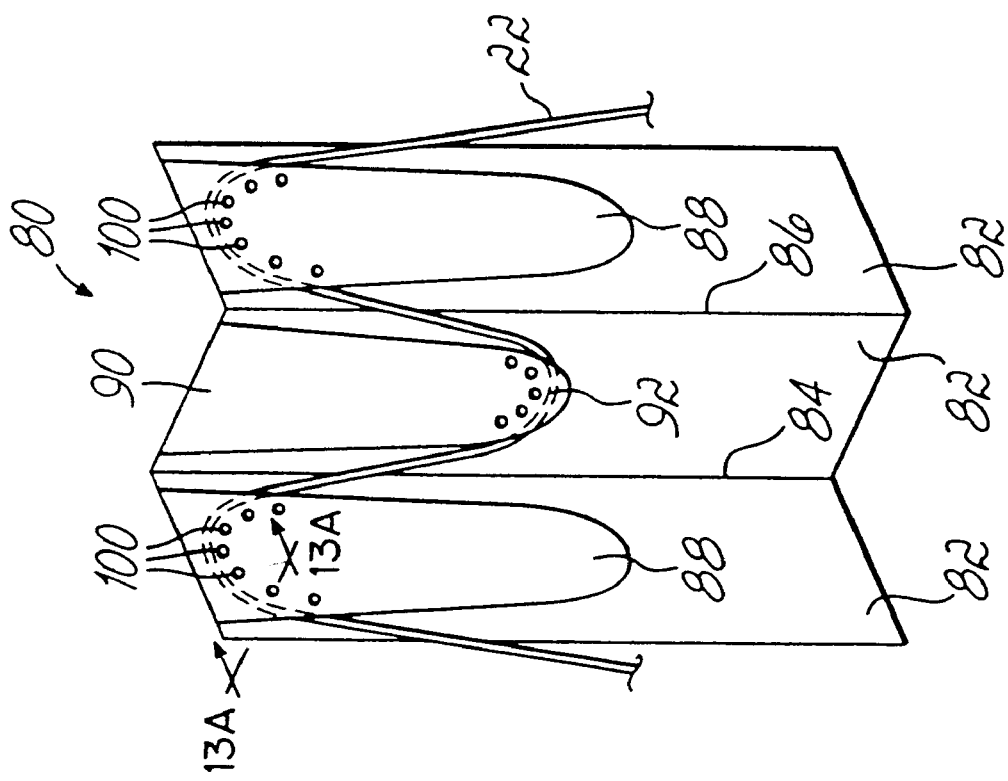

NON-KINKING AND NON-TANGLING SUTURE PACKAGE

The present application is a continuation of PCT Ser. No. PCT/US01/02772 filed on Jan. 26, 2001, which claims the priority of provisional patent application Ser. No. 60/178,577, filed Jan. 26, 2000, now abandoned. The disclosures of each of these prior related applications are hereby fully incorporated by reference herein.

FIELD OF THE INVENTION

The present invention generally relates to packaging for sutures and, more specifically, to disposable packages used during medical procedures to allow ready deployment of the suture as needed by the surgeon or other medical personnel.

BACKGROUND OF THE INVENTION

Surgeons and other medical personnel use sutures on a daily basis. These sutures should be packaged in a manner allowing ready deployment, as necessary, as the need for suturing during surgery or other medical procedure arises. Various types of suture packaging have been proposed in the past and several types currently exist in commercial form. FIGS. 1 and 2 illustrate a suture 10 of the prior art comprised of a suture material 12 and suture needles 14, 16 at affixed opposite ends thereof. Generally, the most commercially successful types of suture packaging have involved uniformly looping the suture material in a figure eight configuration over itself within the package. Suture material 12 is generally formed from natural or synthetic materials that tend to become set into a kinked condition after being folded or looped and compressed for a period of time within the packaging. This characteristic, coupled with the current figure eight packaging techniques, cause the suture material to acquire a certain amount of stored energy much like a compressed spring. As the suture is taken from the package, it tends to come out all at once and, with the stored energy released in this uncontrolled manner, the suture material often becomes intertangled.

Suture 10 is schematically shown in FIG. 1 with the uniform loops 12a expanded for illustration purposes. Typically, these uniform loops 12a are compressed together and sandwiched between paper flaps within a flat, disposable package. Uniform loops 12a tend to become intertangled when removed from current packaging as discussed above, and as shown in FIG. 2, and further tend to create so-called "air knots". Air knots are created when one of the suture needles 14, 16 passes through one or more loops 12a or when loops become intertangled either while they are pulled from the package or after they are pulled from the package. When pulled taught, a knot is formed making the suture 10 unuseable. Also, various folds in the suture packaging can cause sutures 10, and especially fine or small diameter sutures, to hang up or become caught on fractured paper fibers caused by perforated edges. After the suture material 12 is removed from a conventional package, suture 10 does not hang straight as is most desirable, but tends to have significant bends or kinks created where the suture material 12 was looping back and forth within the packaging. Sometimes the suture is stretched or tensioned to remove the kinks before use, but this can result in breaking the suture. In emergency situations or other typical medical procedures, there is no time to allow the suture to relax and straighten. Therefore, the surgeon must use the less than desirable kinked suture.

To overcome various problems in this art, such as those mentioned above, as well as other problems in the art, it would be desirable to provide an improved suture package configured to reduce setting and subsequent kinking of the suture material, while also reducing the instances of loops becoming tangled or forming air knots when the suture is removed from the packaging.

SUMMARY OF THE INVENTION

The present invention therefore provides a suture package with several different features aimed at reducing various problems in this art. As one main feature, the invention provides a package which forms uneven loops, or loops of different length, to prevent the suture loops from becoming tangled and potentially forming air knots when removed from the package. To prevent kinking and to allow withdrawal of the suture in a controlled manner without tangling, the suture material is packaged in an accordion-style packaging material or other package configuration that physically separates adjacent loops of suture material. In the preferred accordion-style package, the suture material transitions over the folds between adjacent subpanels of an accordion-style panel at a gradual obtuse angle, such as an angle approaching a parallel orientation relative to the fold line. Inner folds of the accordion-style packaging are embossed to prevent pinching of the suture material, while outer fold lines are embossed or scored on the backside of the packaging to prevent the suture from hanging up on fractured paper fibers of the accordion-style panel. As used herein, the term "embossing" means applying discreet pressure along a fold line with or without scoring. An internal panel or member, preferably formed into a three-dimensional configuration or, in other words, at least having a three-dimensional thickness, prevents the package from being crushed and thereby pinching the suture material after packaging.

The loops formed along alternating subpanels of the accordion-style panel are initially formed on pins extending through the package from a packaging fixture as explained further below, but are retained by flaps after withdrawal of the pins at the end of the packaging operation. Loops formed on the opposite set of alternating subpanels are received by tabs at the bottom of the package. The tabs create a track for the suture material and slightly wedge the suture material in place. The tabs help prevent kinking and allow the suture material to be pulled from the package in a controlled manner by grasping and pulling the exposed suture needles from respective needle retention elements. Due to the accordion-style of the packaging, the suture material preferably does not fold or lay directly on top of itself. Rather, each loop of the suture material is separated by subpanels of the packaging. This further prevents the loops of suture material from hanging up on each other as they are pulled from the package. Although less desirable, it is also possible to place more than one loop between adjacent subpanels. Further, the transition between the suture material and the suture needle is straight and, therefore, no set or kink is created at this critical transition point.

The package of this invention may be a single suture package or a multi-suture package. For example, respective sutures may be retained on front and back sides of the accordion-style panel. The invention is also applicable to all types of suture material, but is especially advantageous with respect to those materials that easily take on a set. These materials tend to be monofilament sutures and sutures formed from natural gut. The invention is also especially suitable for packaging very fine suture materials, such as those used during cardiac surgery, hand surgery or other procedures using suture sizes of, for example, 6-0, 7-0 or higher. The foldable flaps in the suture packaging of this invention and the tabs create a certain amount of drag on the suture when the packaging is in its fully closed condition. This drag helps the suture to pull out in a controlled manner by causing the suture to retain its looped shape under each successive flap and tab as the suture material is being pulled out of the package.

In one general embodiment, the suture package has two long sides and two shorter ends. The suture needles are positioned for grasping preferably by exposing them at one of the ends and are removed with the suture material by pulling the suture from that end. Thus, the pulling occurs in a direction generally parallel to the length of the subpanels and the fold lines, if any, therebetween. In another embodiment, the suture needles are positioned for grasping preferably by exposing them along the length of one of the long sides of the suture package. Therefore, in this embodiment, the suture is pulled from the package in a direction generally transverse to the length of the subpanels and any fold lines therebetween. In this second embodiment, at least one advantage is provided by the fact that the suture material will not ride along the lengthwise edges of the subpanels during its removal. This can help prevent snagging and potential damage to the suture material caused by roughness along the lengthwise edges of the subpanels.

Generally, the method of packaging a suture in accordance with the invention includes looping a suture back-and-forth on a series of subpanels and superimposing the subpanels on each other such that adjacent loops of the suture are retained between adjacent, superimposed subpanels. Respective ends of the suture, which typically include needles attached thereto, are positioned for grasping in an accessible location. The superimposed subpanels are secured together in the form of a package either before or after the respective ends are positioned in the accessible location.

More specifically, the accordion-style panel is stretched out into a flat condition with the flaps containing the assembly pin holes flipped away from the accordion-style panel. The assembly pin holes of alternating subpanels on the accordion-type panel receive the assembly pins from the fixture. One of the suture needles is retained in a suitable needle retaining element at one end of the package and the suture material is looped back and forth over the assembly pins and then around the oppositely disposed tabs on each of the adjacent subpanels until reaching the final suture retaining element at the opposite end of the package. The assembly pins and the oppositely disposed tabs preferably force the suture material into curves of substantially constant radii to prevent sharp transitions in directions which may result in kinks. When this part of the packaging operation is complete, the flaps which were previously folded out of the way are folded back down over the pins. The pins are then withdrawn from the holes in the package by a suitable reciprocating feature of the packaging fixture and the accordion-style panel is folded together. The stiff internal panel is folded over first followed by the outside panel which is secured around the outside of the folded, accordion-style panel and retained in place. As one additional, alternative feature, the flaps which receive the pins may also be releasably connected to the underlying subpanels, for example, by forming perforations through the flap and underlying subpanel. This can be used to retain the suture loop in place beneath the flap until a user pulls the suture material and thereby breaks the connection between the flap and the underlying subpanel. At least one panel may have slots for receiving the assembly pins in an adjustable manner. This allows for adjustment in the length of, for example, the final loop of suture material to accommodate inconsistent lengths of different sutures during the packaging operation and allow the needle to reach and be retained in an accessible position with a straight transition between the needle and the suture material.

These and other objects, advantages, and features of the invention will become more readily apparent to those of ordinary skill in the art upon review of the following detailed description of the preferred embodiments, taken in conjunction with the accompanying drawings.

BRIEF DESCRIPTION OF THE DRAWINGS

FIG. 4 is a schematic, perspective view of the accordion-style suture package constructed in accordance with the preferred embodiment of this invention.

FIG. 4A is a cross sectional view taken along line 4A—4A of FIG. 4.

FIG. 5 is a side elevational view of the accordion-style package.

FIG. 6 is a perspective view generally showing the gradual transition of the suture material over a fold line of a package constructed in accordance with the invention.

FIG. 7 is a schematic illustration of an embossed inner fold line between two panels of the suture package of this invention.

FIG. 8 is a schematic view of a scored, outer fold line between two panels of the package of this invention.

FIG. 13 is a perspective view partially showing an alternative suture package.

FIG. 13A is a cross sectional view taken along line 13A—13A of FIG. 13.

DETAILED DESCRIPTION OF THE PREFERRED EMBODIMENTS

Figure 3:
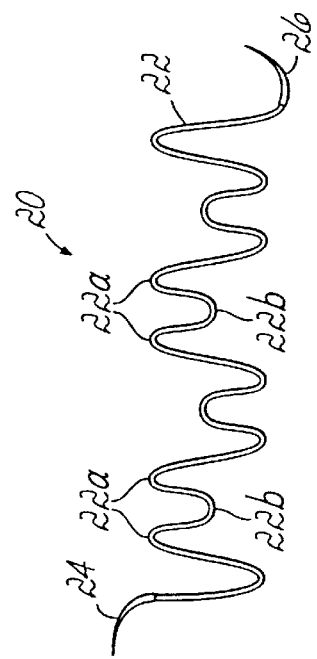
FIG. 3 illustrates a suture in accordance with the present invention having nonuniform loops of different lengths.
Figure 2:
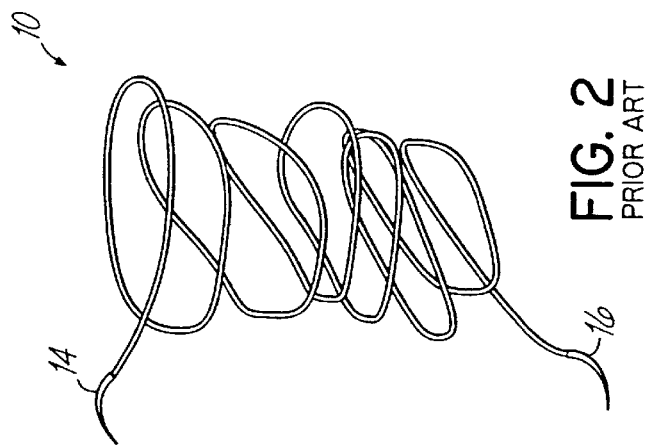
FIG. 2 illustrates the suture of FIG. 1 tending to become tangled in accordance with the prior art.
Figure 1:
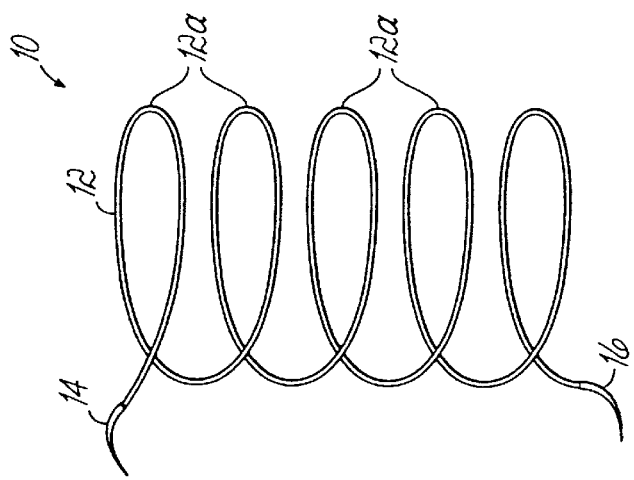
FIG. 1 schematically illustrates a conventional suture in slightly expanded form.

FIG. 3 illustrates a suture 20 after packaging in accordance with the present invention. Suture 20 includes a suture material or thread 22 having suture needles 24, 26 at opposite ends and formed into a series of non-uniform loops 22a, 22b. These loops do not tend to become tangled or form air knots when removed from packaging of the present invention. In addition, these loops do not form nearly the permanent or semi-permanent set formed by current and past suture packaging methods.

FIG. 4 illustrates an unfolded accordion-style package 30 constructed in accordance with the preferred embodiment. Package 30 includes an accordion-style paper panel 32 having a series of folded subpanels 32a. Although paper is the currently preferred material for the various elements of package 30, other materials may be used as well. Subpanels 32a are separated by outer folds 34 and inner folds 36. Alternating panels 32a include integrated or otherwise connected flaps 38 which fold over from the top edge of panel 32 to apply slight compression to suture material 22 after the packaging operation is complete. Holes 40 are provided in these alternating subpanels 32a and a like series of three holes 42 are provided in the corresponding flaps 38. When flaps 38 are folded over, holes 40 register in alignment with holes 42. Holes 40 receive respective pins (not shown) extending from a suitable packaging fixture to allow suture material 22 to be directed in the manner shown in FIG. 4. Respective tabs 44 angle slightly upward from tabs 39 affixed to the opposite alternating series of subpanels 32a and receive lower loops of the suture material 22. This is more specifically shown in FIG. 4A. Tabs 44 are at staggered distances from the respective series of holes 40 to create the uneven loop pattern discussed above and shown in FIG. 3. An inner stiff panel 50 in package 30 has a three-dimensional configuration formed by a lip 52 for purposes to be discussed in greater detail below. An opening 54 is provided in flap 50 to expose needle 24 to allow removal of suture 20 by the user. An outer flap 60 is provided to enclose and secure the entire package in its folded condition (FIG. 9).

FIGS. 5, 7 and 8 illustrate the accordion-style panel 32 as well as outer fold lines 34 and inner fold lines 36. As shown best in FIG. 7, inner fold lines 36 are embossed to prevent adjacent subpanels 32a from pinching suture material 22 in the folded condition. Also, outer fold lines 34 are scored on the back side as opposed to the front side thereof to prevent suture material 22 from hanging up or becoming caught on fractured paper fibers when directed over the fold line 34, as shown in FIG. 6.

Figure 9:
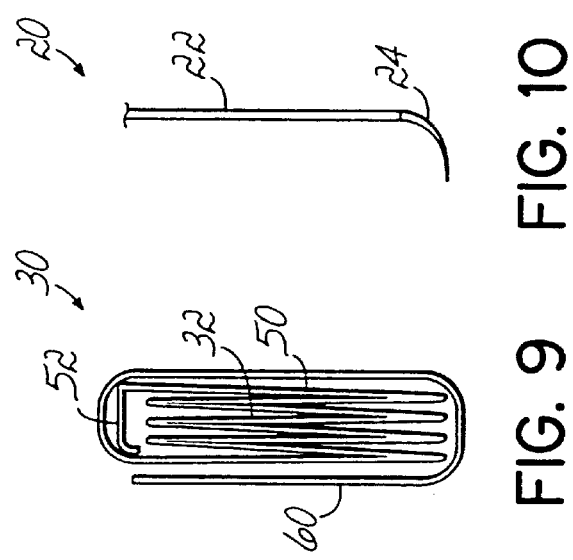
FIG. 9 is a cross sectional view of the accordion-style package showing the stiff inner panel providing support to the interior accordion-style panels.

FIG. 9 illustrates the package 30 in its fully folded and secured condition. In this illustration, it should be noted that stiff panel 50 and lip 52 prevent package 30 from being significantly crushed and thereby pinching the suture after packaging. This feature further inhibits kinking or causing suture 20 to hang up as it is withdrawn from package 30.

Figure 10:
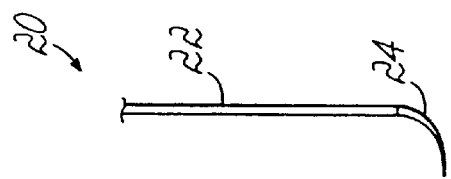
FIG. 10 is a schematic illustration of the straight transition between the suture material and the suture needle.

FIG. 10 illustrates a portion of suture 20 illustrating the transition between suture material 22 and needle 24. In accordance with the invention, this transition zone is substantially straight and, due to the packaging principles expressed herein, needle 24 is not permanently or semi-permanently set into a kinked or angled position with respect to suture material 22.

Figure 11:
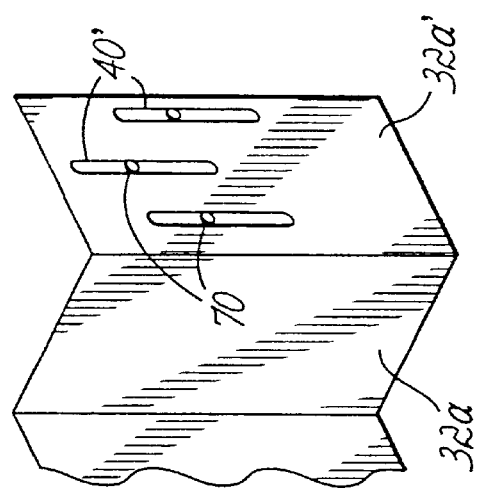
FIG. 11 is a perspective view showing a panel with slots allowing length adjustment for inconsistent suture lengths.

FIG. 11 illustrates an alternative subpanel 32a' which may be used in the end subpanel, for example, adjacent flap 60 (FIG. 4). Subpanel 32a' includes elongated slots 40' adapted to carry adjustable pins 70 during the packaging operation. For example, pins 70 may extend upwardly from a fixture (not shown) and may adjust in position along the length of slots 40' to adjust and accommodate the length of a particular suture.

Figure 12:
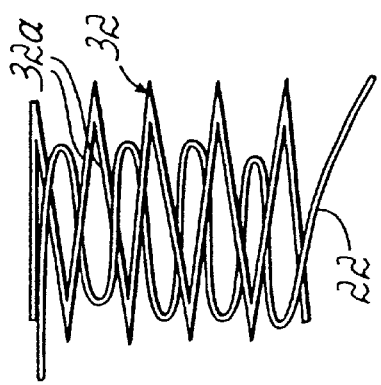
FIG. 12 is a schematic illustration of the accordion-style package showing separation between the suture loops within the package.

FIG. 12 schematically illustrates accordion-style panel 32 and suture material 22 directed in a generally serpentine fashion over adjacent subpanels 32a. Subpanels 32a prevent adjacent loops of suture material 22 from contacting one another when accordion-style panel 32 is folded as shown in FIG. 12 and then compressed as shown in FIG. 9.

As understood from reviewing FIG. 4, the packaging operation involves unfolding accordion-style panel 32 into a flat condition and placing holes 40 over separate series of extendable and retractable pins (not shown) associated with a suitable fixture. Once panel 32 is stretched out into this flat condition and retained on the fixture pins, suture 20 may be successively directed around the pins extending through holes 40 and also around tabs 44 as shown in the drawing. Once this is accomplished, flaps 38 are folded over such that the pins extend through holes 42. The pins are then retracted and accordion-style panel 32 is immediately folded into its compressed condition shown in FIG. 9. Flap 50 is folded over first and then flap 60 is secured around the outside thereof, such as by using a suitable adhesive. To withdraw suture 20, the user preferably grasps both of the exposed needles 24, 26 and pulls suture 20 from package 30.

FIGS. 13 and 13A illustrate an alternative accordion-style package 80 shown in partial form, with suture material 22 directed therethrough in a similar fashion to the previously described embodiment. Package 80 includes a plurality of accordion-style folded subpanels 82 connected by fold lines 84, 86. Alternating subpanels 82 have flaps 88 folded over from upper ends thereof, while subpanels 82 therebetween include folded over flaps 90 affixed to the respective subpanel 82 to form a tab 92 in a manner and for reasons similar to the previously described embodiment. In this embodiment, flaps 88 are perforated into subpanels 82 as shown in FIG. 13A and along a curved path following the path of suture material 22. This forms a track to retain suture material 22 in the intended looping configuration above the perforations 100. As suture material 22 is pulled downwardly from package 80, as viewed in FIG. 13, the connections between subpanels 82 and flaps 88 formed by perforations 100 will break and allow suture material to be withdrawn from package 80 in the previously described controlled manner.

Figure 14:
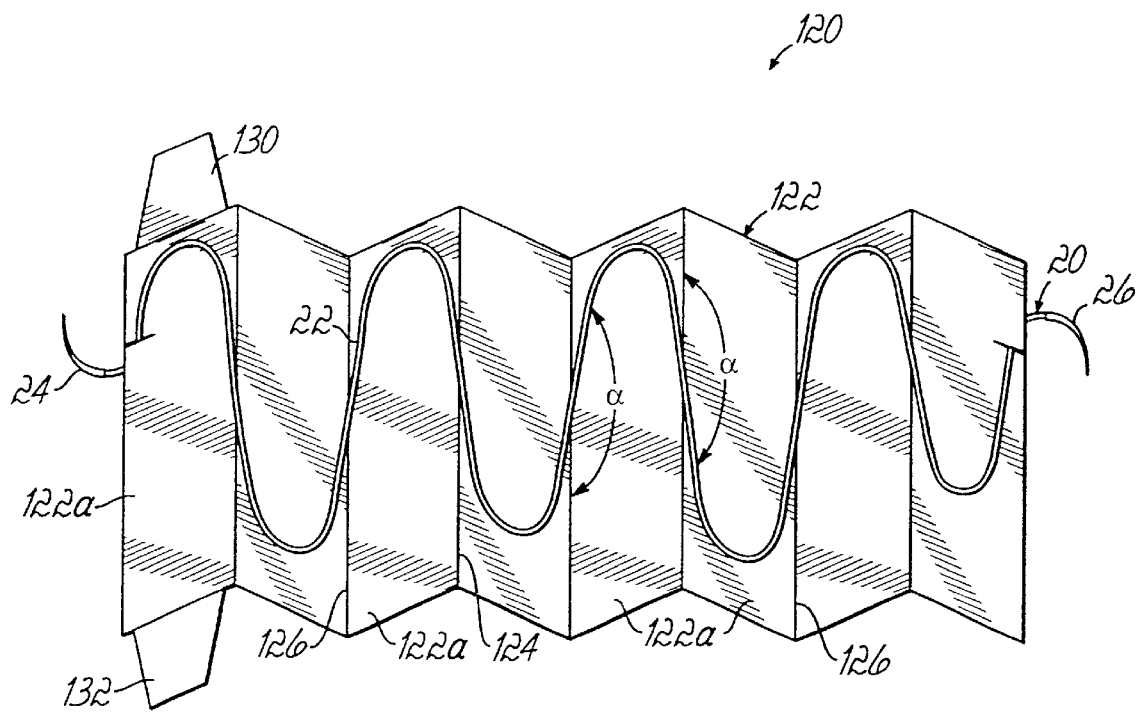
FIG. 14 is a perspective view of another accordion-style suture package constructed in accordance with the invention.
Figure 14A:
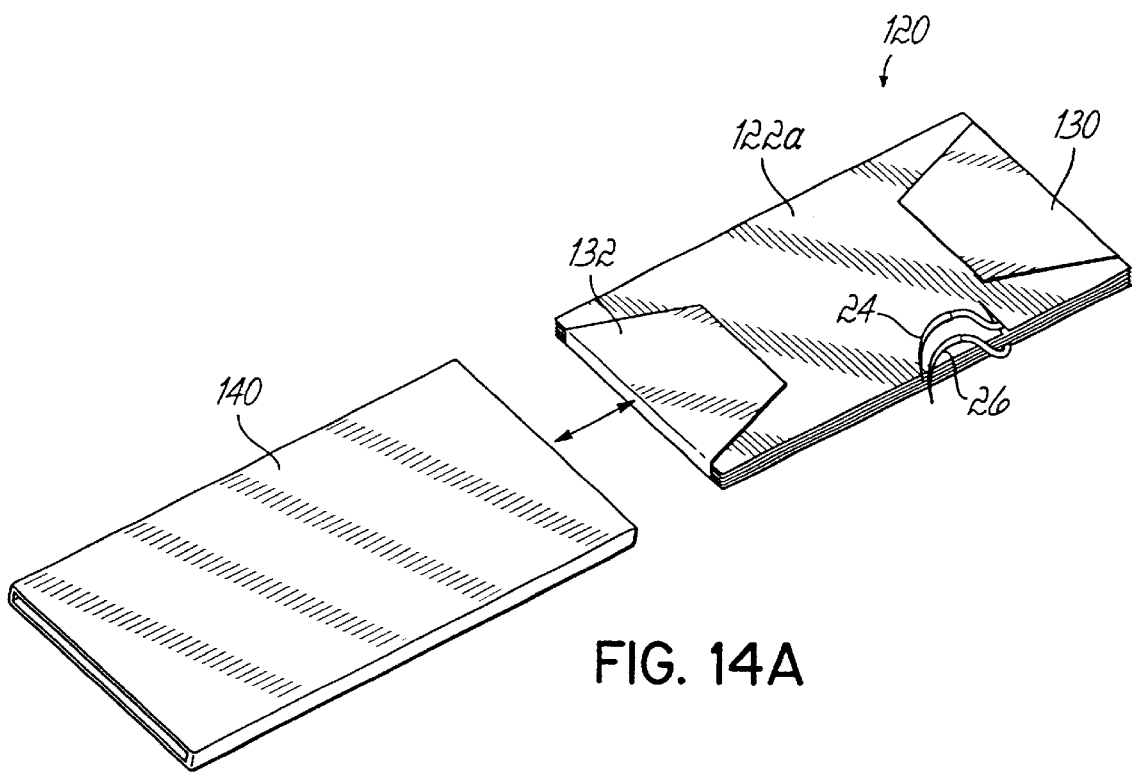
FIG. 14A is a perspective view of the suture package shown in FIG. 14, but illustrating the package in a folded condition and removed from a holder.
Figure 15:
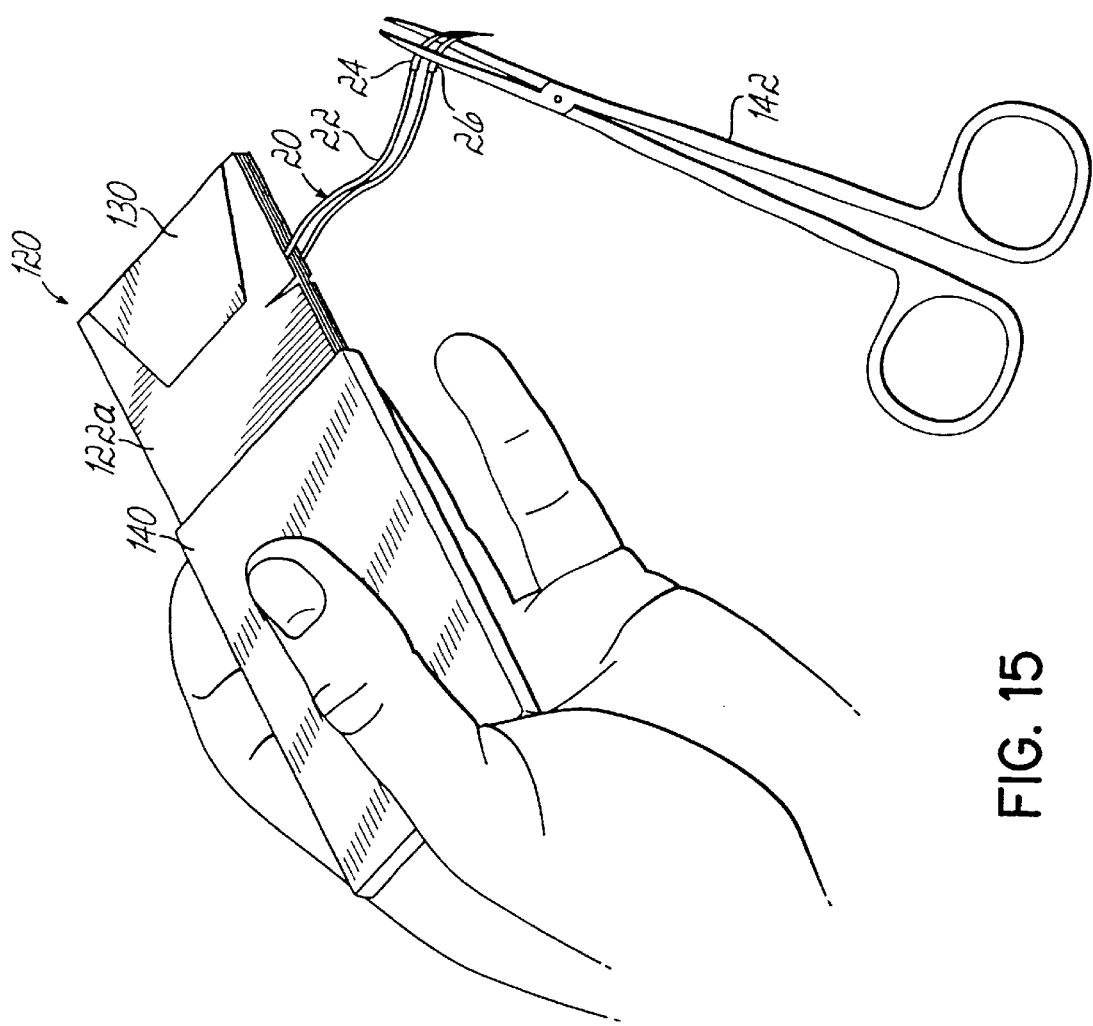
FIG. 15 is a perspective view illustrating the suture package partially removed from the holder and removal of the suture therefrom.

FIGS. 14, 14A and 15 illustrate an alternative embodiment of a suture package 120. In these figures, like reference numerals indicate like structure or elements with other embodiments of the invention. Suture 20 is again retained on an accordion-style panel 122 comprised of a plurality of subpanels 122a. Suture material 22 includes suture needles 24, 26 at opposite ends and is formed into a series of loops placed on adjacent subpanels 122a as in previous embodiments. Other features of the previous embodiments may or may not also be included in this embodiment. Subpanels 122a are separated by folds 124, 126 and suture material 122 crosses these folds at an angle a which is obtuse and preferably approaches parallel relative to the fold lines 124 or 126. For example, suture material 30 is ideally within about 30° of parallel (angle $\alpha \geq 150°$) to fold lines 124 or 126 as it crosses from one subpanel to the next. The main difference between suture package 120 and the suture packages of the previous embodiments is that suture needles 24, 26 exit suture package 120 along a side edge of package 120, as best shown in FIG. 14a and 15, instead of exiting at one end. This allows suture 20 to be pulled out essentially in a perpendicular direction to the fold lines 124, 126 as shown in FIG. 15. Therefore, suture material 22 is not dragged along fold lines 126.

It has been found that outer fold lines 126 may have discontinuities which tend to snag on suture material 22 if suture material 22 is pulled out from one end of package 120 as opposed to being pulled out along the long side as shown in FIG. 15. Thus, this embodiment prevents this snagging and any potential damage to the suture material 22 which results therefrom. As further shown in FIGS. 14 and 14A, a pair of paper flaps 130, 132 may be used to secure panel 122 in its folded condition, such as by adhesively securing flaps 130, 132 in the positions shown in FIG. 14A. Package 120 may then be placed in a suitable holder, such as a flat hollow paper holder 140 for final packaging and shipping purposes. As an alternative, this separate outer package portion or holder 140 may be an integral member such as a flap. As further shown in FIG. 15, when suture package 120 is ready for use, package 120 is partially or fully removed from holder 140 and a suitable surgical implement 142 is used to pull suture 20 from package 120. This embodiment retains the advantages of the previously described embodiments in terms of providing a non-kinking and non-tangling suture, and further prevents any potential suture damage or other difficulties as the suture 20 is quickly removed at the point of use.

While the present invention has been illustrated by a description of a preferred embodiment and while this embodiment has been described in some detail, it is not the intention of the Applicants to restrict or in any way limit the scope of the appended claims to such detail. Additional advantages and modifications will readily appear to those skilled in the art. The various features of the invention may be used alone or in numerous combinations depending on the needs and preferences of the user. This has been a description of the present invention, along with the preferred methods of practicing the present invention as currently known. However, the invention itself should only be defined by the appended claims, wherein

We claim:

1. A suture package comprising:
    an accordion style panel having at least three subpanels with adjacent subpanels folded in opposite directions; and
    a suture looping back and forth on one side of the accordion style panel to form a plurality of loops on the one side of the panel, each of the plurality of loops being placed upon a different one of the subpanels when the accordion style panel is in an unfolded condition.

2. The suture package of claim 1 further comprising:
    a series of flaps connected at one end of alternating subpanels, each said flap being foldable onto the suture loop placed upon the corresponding one of the alternating subpanels.

3. The suture package of claim 2, wherein each of said flaps is connected in a releasable manner to a face of the corresponding one of the alternating subpanels to retain the suture loops in place until a user pulls the suture from the package.

4. The suture package of claim 3, wherein the flaps are connected in said releasable manner by perforations extending through the flaps and the alternating subpanels.

5. The suture package of claim 2 further comprising:
    a tab connected to a second series of alternating subpanels between the subpanels having said flaps and adapted to receive respective loops of the suture.

6. The suture package of claim 1 further comprising a support member formed in three dimensions and retained in the package in a fully folded condition of the panel to prevent pinching of the suture between the subpanels.

7. The suture package of claim 1, wherein the suture is directed over fold lines of the accordion style panel at an obtuse angle with respect to the fold line.

8. The suture package of claim 7, wherein the angle is within about 30 degrees of parallel to the fold line.

9. The suture package of claim 1, wherein outer fold lines of the accordion style panel are embossed on a back side thereof opposite to the side that receives the suture.

10. The suture package of claim 1, wherein inner fold lines of the accordion style panel are embossed to extend sway from the side that receives the suture.

11. The suture package of claim 1, wherein at least alternating subpanels include respective holes for receiving pins adapted to temporarily guide the suture into the loops.

12. The suture package of claim 11, wherein at least one set of holes in one subpanel comprises respective slots to allow lengthwise adjustment of a suture loop for accommodating sutures of different length.

13. The suture package of claim 1, wherein the adjacent loops are of different lengths to reduce tangling of said suture upon withdrawal and removal from the package.

14. The suture package of claim 1 further comprising needle retention elements for holding said needles with straight transitions between the needles and the suture material.

15. The suture package of claim 1, wherein the accordion style panel includes opposite ends arid opposite side edges in a fully folded condition of the panel and the suture includes at least one needle fixed thereto, the needle being accessible at one of the opposite ends to allow removal of the suture in a direction generally parallel to respective fold lines extending between the adjacent subpanels.

16. The suture package of claim 1, wherein the accordion style panel includes opposite ends and opposite side edges in a fully folded condition of the panel and the suture includes at least one needle fixed thereto, the needle being accessible at one of the opposite side edges to allow removal of the suture in a direction transverse to respective fold lines extending between the adjacent subpanels.

17. A suture package comprising:
    at least three subpanels;
    a suture looping back and forth on respective faces of the subpanels to form a plurality of loops on the respective faces of the subpanels, each of the plurality of loops being placed upon a different one of the subpanels; and
    an outer package portion securing the at least three of subpanels together in facing relation.

18. The suture package of claim 17, wherein the subpanels include opposite ends and opposite side edges which are longer than the opposite ends, and the suture includes at least one needle fixed thereto, the needle being accessible at one of the opposite ends to allow removal of the suture in a direction generally parallel to the opposite side edges.

19. The suture package of claim 17, wherein the subpanels include opposite ends and opposite side edges which are longer than said opposite ends, and the suture includes at least one needle fixed thereto, the needle being accessible at one of the opposite side edges to allow removal of the suture in a direction transverse to the opposite side edges.

20. The suture package of claim 17 further comprising:
    a series of flaps connected at one end of alternating subpanels, each said flap being foldable onto the suture loop placed upon the corresponding one of said subpanels.

21. The suture package of claim 20, wherein each of said flaps is connected in a releasable manner to a face of the corresponding one of the alternating subpanels to retain the suture loops in place until a user pulls the suture from the package.

22. The suture package of claim 21, wherein the flaps are connected in said releasable manner by perforations extending through the flaps and the alternating subpanels.

23. The suture package of claim 20 further comprising:
a tab connected to a second series of alternating subpanels between the subpanels having said flaps and adapted to receive respective loops of the suture.

24. The suture package of claim 17 further comprising a support member formed in three dimensions and retained in the package in a fully folded condition of the panel to prevent pinching of the suture between the subpanels.

25. The suture package of claim 17, wherein the suture is directed over lengthwise edges of the subpanels at obtuse angles with respect to the lengthwise edges.

26. The suture package of claim 25, wherein the angle is within about 30 degrees of parallel to the respective lengthwise edge.

27. The suture package of claim 17, wherein at least alternating subpanels include respective holes for receiving pins adapted to temporarily guide the suture into the loops.

28. The suture package of claim 27, wherein at least one set of holes in one subpanel comprises respective slots to allow lengthwise adjustment of a suture loop for accommodating sutures of different length.

29. The suture package of claim 17, wherein the adjacent loops are of different lengths to reduce tangling of said suture upon withdrawal and removal from the package.

30. The suture package of claim 17 further comprising needle retention elements for holding said needles with straight transitions between the needles and the suture material.

31. A method of packaging a suture, the method comprising:
temporarily retaining an accordion-style panel on a plurality of retractable pins by extending said pins through holes in alternating subpanels of the accordion-style panel;
looping a suture along the subpanels and around each set of pins on the alternating subpanels;
looping the suture further around a suture retainer disposed on each subpanel between the alternating panels;
folding respective flaps downwardly over the pins and the loops of suture material on the alternating subpanels;
retracting the pins; and
folding the accordion-style panel into a fully folded condition with adjacent suture loops being separated by adjacent subpanels.

32. A method of packaging a suture, the method comprising:
looping a suture back and forth on respective faces of at least three subpanels to form a plurality of loops on the respective faces of the subpanels, each of the plurality of loops being placed upon a different one of the subpanels;
superimposing the subpanels on each other
positioning respective ends of the suture in en accessible location for grasping; and
securing the superimposed subpanels together in the form of a package.

33. The method of claim 32, wherein the subpanels are formed as portions of an accordion style panel and superimposing the subpanels further comprises folding the subpanels together with the suture extending over respective fold lines between the adjacent subpanels.

34. The method of claim 32, wherein the respective ends of the suture each include a needle secured thereto and the superimposed subpanels include two lengthwise side edges and two ends shorter than the side edges, and the step of exposing the respective ends further comprises exposing the needles at one of the two ends.

35. The method of claim 34 further comprising:
pulling the suture out of the package in a direction generally parallel to the side edges.

36. The method of claim 33, wherein the respective ends of the suture each include a needle secured thereto and the superimposed subpanels include two lengthwise side edges and two ends shorter than the side edges, and the step of exposing the respective ends further comprises exposing the needles at one of the two side edges.

37. The method of claim 36 further comprising:
pulling the Suture Out of the package in a direction transverse to the side edges.

* * * * *

UNITED STATES PATENT AND TRADEMARK OFFICE
CERTIFICATE OF CORRECTION

PATENT NO.   : 6,659,270 B2
DATED        : December 9, 2003
INVENTOR(S)  : Warren P. Williamson IV et al.

It is certified that error appears in the above-identified patent and that said Letters Patent is hereby corrected as shown below:

Column 6,
Line 52, change "a" to -- α --.

Column 8,
Line 8, change "sway" to -- away --.
Line 24, change "arid" to -- and --.
Line 43, delete "of".

Column 10,
Line 11, change "other" to -- other; --
Line 12, change "en" to -- an --.
Line 30, change "33" to -- 32 --.
Line 37, change "Suture Out" to -- suture out --.

Signed and Sealed this

Twenty-fourth Day of May, 2005

JON W. DUDAS
*Director of the United States Patent and Trademark Office*